(12) United States Patent  
Weber et al.

(10) Patent No.: US 8,025,637 B2
(45) Date of Patent: Sep. 27, 2011

(54) MEDICAL BALLOONS AND PROCESSES FOR PREPARING SAME

(75) Inventors: Jan Weber, Maple Grove, MN (US); Scott Schewe, Eden Prairie, MN (US); Robert E. Burgmeier, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1215 days.

(21) Appl. No.: 10/622,621

(22) Filed: Jul. 18, 2003

(65) Prior Publication Data

US 2005/0015046 A1   Jan. 20, 2005

(51) Int. Cl.
*A61M 31/00* (2006.01)
*A61M 37/00* (2006.01)

(52) U.S. Cl. .............. 604/103.06; 604/103.09

(58) Field of Classification Search ........... 604/96.01, 604/915, 916, 103.04, 103.06, 103.07, 103.08, 604/103.01, 103.02, 103.09; 606/192, 194, 606/198, 1.98; 623/1.11; 264/129; 428/474.4
See application file for complete search history.

(56) References Cited

U.S. PATENT DOCUMENTS

| | | | |
|---|---|---|---|
| 2,481,488 A | 9/1949 | Auzin | 156/242 |
| 2,690,595 A | 10/1954 | Raiche | 18/58.7 |
| 3,304,353 A | 2/1967 | Harautuneian | 264/515 |
| 4,327,734 A * | 5/1982 | White, Jr. | 606/195 |
| 4,497,074 A | 2/1985 | Rey et al. | 623/1.24 |
| 4,661,095 A | 4/1987 | Taller et al. | 604/103 |
| 4,737,219 A | 4/1988 | Taller et al. | 156/215 |
| 4,906,423 A | 3/1990 | Frisch | |
| 4,929,403 A | 5/1990 | Audsley | |
| 4,952,357 A | 8/1990 | Euteneuer | 264/129 |
| 4,976,720 A | 12/1990 | Machold et al. | 606/194 |
| 5,000,734 A * | 3/1991 | Boussignac et al. | 604/103.06 |
| 5,049,132 A * | 9/1991 | Shaffer et al. | 604/101.02 |
| 5,100,381 A | 3/1992 | Burns | 604/96 |
| 5,145,942 A | 9/1992 | Hergenrother et al. | 528/353 |
| 5,184,874 A | 2/1993 | Olson | 301/64.7 |
| 5,207,700 A | 5/1993 | Euteneuer | 606/194 |
| 5,219,120 A | 6/1993 | Ehrenberg et al. | 239/11 |
| 5,223,205 A | 6/1993 | Jackowski et al. | 264/521 |
| 5,304,197 A | 4/1994 | Pinchuk et al. | 606/194 |
| 5,320,634 A | 6/1994 | Vigil et al. | 606/159 |
| 5,409,458 A | 4/1995 | Khairkhahan et al. | 604/103.08 |
| 5,439,443 A | 8/1995 | Miyata et al. | 604/96 |
| 5,449,371 A | 9/1995 | Pinchuk et al. | 606/194 |
| 5,499,980 A | 3/1996 | Euteneuer | 606/28 |
| 5,549,553 A | 8/1996 | Ressemann et al. | 604/103.08 |
| 5,738,653 A | 4/1998 | Pinchuk et al. | 604/96 |
| 5,772,864 A | 6/1998 | Moller et al. | 205/73 |

(Continued)

FOREIGN PATENT DOCUMENTS

DE    1810311    2/1970

(Continued)

*Primary Examiner* — Christopher Koharski
(74) *Attorney, Agent, or Firm* — Vidas, Arrett & Steinkraus, P.A.

(57) ABSTRACT

A medical device such as a catheter, stent or balloon, is formed by depositing a radiation curable composition on a form made of ice or wax. The deposited composition may be cured by irradiation, suitably with UV light. Complex structures can be built up if the deposition or curing is achieved imagewise. Compositions which photocure to polyester, polyamide or polyimide may be employed. A particular structure is a balloon for a rapid exchange catheter which has a guide wire lumen passing through the balloon cone walls.

9 Claims, 6 Drawing Sheets

U.S. PATENT DOCUMENTS

| | | | |
|---|---|---|---|
| 5,797,877 A | 8/1998 | Hamilton et al. | 604/96 |
| 5,833,657 A | 11/1998 | Reinhardt et al. | 604/96 |
| 5,855,753 A | 1/1999 | Trau et al. | 204/484 |
| 5,908,406 A | 6/1999 | Ostapchenko et al. | 604/96 |
| 6,007,517 A * | 12/1999 | Anderson | 604/103.04 |
| 6,024,722 A | 2/2000 | Rau et al. | 604/96 |
| 6,033,547 A | 3/2000 | Trau et al. | 204/622 |
| 6,086,556 A | 7/2000 | Hamilton et al. | 604/96 |
| 6,110,142 A | 8/2000 | Pinchuk et al. | 604/96 |
| 6,120,523 A * | 9/2000 | Crocker et al. | 606/192 |
| 6,132,824 A * | 10/2000 | Hamlin | 428/35.2 |
| 6,156,254 A | 12/2000 | Andrews et al. | 264/231 |
| 6,224,803 B1 | 5/2001 | Tiernan | 264/166 |
| 6,328,710 B1 | 12/2001 | Wang et al. | 604/96.01 |
| 6,486,230 B1 | 11/2002 | Meador | 522/180 |
| 6,500,146 B1 | 12/2002 | Pinchuk et al. | 604/96.01 |
| 6,500,148 B1 | 12/2002 | Pinchuk et al. | 604/103.11 |
| 6,663,646 B1 * | 12/2003 | Shah | 606/192 |
| 7,331,933 B2 * | 2/2008 | Steadham et al. | 604/96.01 |
| 2001/0003796 A1 * | 6/2001 | Yang et al. | 604/265 |
| 2003/0018387 A1 | 1/2003 | Schuessler | 623/8 |
| 2003/0197308 A1 | 10/2003 | Montoya | |

FOREIGN PATENT DOCUMENTS

| | | |
|---|---|---|
| DE | 4223991 | 2/1993 |
| DE | 19534836 | 3/1997 |
| EP | 1234647 | 8/2002 |
| EP | 1393769 | 3/2004 |
| FR | 2634413 | 1/1990 |
| GB | 773971 | 5/1957 |
| JP | 62135325 | 6/1987 |
| JP | 3248822 | 11/1991 |
| JP | 09140800 | 7/1994 |
| JP | 06190494 | 6/1997 |
| WO | 89 10786 | 11/1989 |
| WO | WO 02068167 | 9/2002 |
| WO | WO 03000480 | 1/2003 |

* cited by examiner

Fig.1
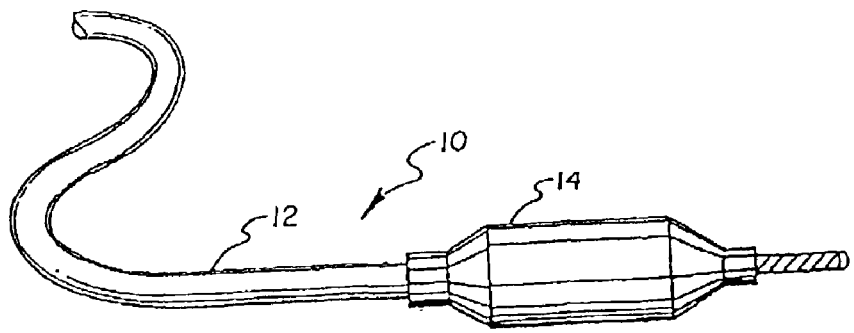
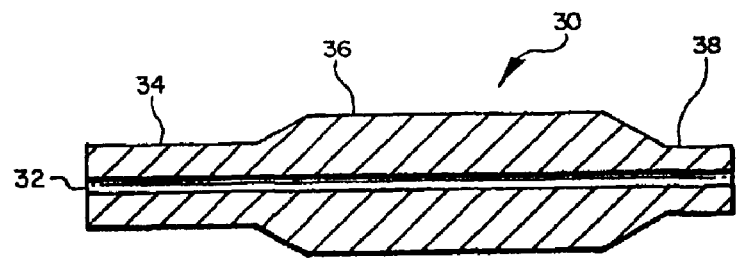
Fig.2A
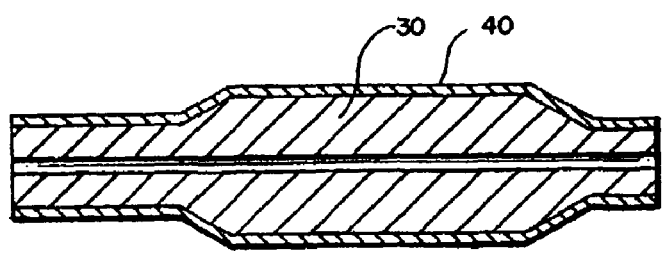
Fig.2B

MEDICAL BALLOONS AND PROCESSES FOR PREPARING SAME

BACKGROUND OF THE INVENTION

Many medical devices comprising polymers, such as diagnostic and balloon catheters, are currently being manufactured utilizing conventional thermoplastic polymer thermoforming techniques such as extrusion, injection molding, stretch blow molding, and the like. Within these processes, one softens or melts the polymer and reshapes it into the desired shape. Although these thermoforming processes are well developed, pressures exist to shrink the size of such medical products. At the same time the diversity of local functional properties within the device is increasing. Consequently, an increasing number of complex processing steps have to be taken to get to the desired result.

Balloon molding from thermoplastic polymer compositions comprising reinforcements is difficult due to the fact that most types of reinforcing agents are unlikely to deform during the blow molding process. Dip molding balloons is possible, but due to the fact the inner shape has to be removed from within the balloon, this is not the most suitable way to produce a reinforced balloon.

High tensile strengths are important in angioplasty balloons because they allow for the use of high pressure in a balloon having a relatively small wall thickness. High pressure is often needed to treat some forms of stenosis. Small wall thicknesses enable the deflated balloon to remain narrow, making it easier to advance the balloon through the arterial system. Similar factors are important in catheter shaft materials.

One of the disadvantages of blow molding balloons is that the cone sections have a thicker wall than the central section. This results in a large balloon profile during folding. A variety of techniques have been offered to reduce cone thickness, but they are not always suitable for a given balloon.

Because of these factors, fabrication techniques for such device components are not adequate to keep reducing size, increasing device complexity, and/or implementing new devices. Consequently there is a need for new fabrication techniques to provide a wider range of local functional properties at the same time allow further size reductions.

Curable compositions, dispensed or applied in liquid form, and subsequently cured have some uses in conventional fabrication of catheter devices, typically in adhesive or coating applications. However, prior to the inventions described herein they have not obtained widespread use.

Devices formed of cured polyimide materials have been described in several documents. Polyimide polymers, known for their high strength at very high temperatures are typically formed by heating polyamide-acid precursor polymer material to a curing temperature where amide and acid groups along the polymer condense to form cyclic imide groups in the backbone polymer chain. This technique is used to form balloons in Euteneuer, U.S. Pat. No. 4,952,357. This fabrication method, however, is unsuited to many device forming applications because of the high temperatures required for curing the polyimide. Further, while polyimide has excellent strength properties, the resulting polymers have relatively poor flexibility, elongation and softness. Still further, the manufacturing procedure uses HF to dissolve a glass substrate upon which the polyamide-acid is formed by deposition from solution. The glass substrate formation and subsequent HF destruction thereof is a relatively dangerous and expensive process. Polyimide tubing used for catheter shafts is described in U.S. Pat. No. 4,976,720, Machold et al, but with no discussion of how it is made.

U.S. Pat. No. 5,100,381, Burns, describes angioplasty catheters with shaft portions made of polyimide or polyimide-polytetrafluoroethylene composite material.

U.S. Pat. No. 6,024,722, Rau et al, applies thermoplastic polyimide to the art of balloon catheter construction, i.e., to catheter shafts, guide catheters, infusion catheters and balloons. Use of this material, however, is subject to the same limitations already recognized for the general class of thermoplastic polymers.

U.S. Pat. No. 5,145,942, Hergenrother, et al, describes methyl-substituted polyimide polymers which are thermoplastic, but curable to a crosslinked state by irradiation with UV or exposure to temperatures in excess of 275° C. The UV irradiation process, however, appears to be very slow (100 hrs at 0.21 watts/cm$^2$ to cure films of 1.7 and 2.4 mils (0.04-0.06 mm). Thus use of this material for forming medical devices appears to offer few or no benefits compared to other polyimides, while at the same time incurring further processing disadvantages.

In addition to condensation from polyamide-acid polymers, it has been proposed to form a polyimide from a bismaleimide compound by Diels Alder cycloaddition, however these reactions are also run at temperatures in excess of 200° C. More recently it has been proposed to prepare polyimides by diene cycloadditions which are catalyzed by UV irradiation, near or even below ambient temperatures.

SUMMARY OF THE INVENTION

The present invention, in one aspect, pertains to processes for forming articles, particularly medical devices, from radiation curable compositions in which pattern-wise curing is used to form the device or coatings thereon. The devices may be polymer devices, or metal or ceramic devices containing polymer surfaces (coatings). In a further aspect, the invention pertains to a device so formed.

An aspect of the invention is the use of ice (frozen water), wax, polyvinyl alcohol, or another readily fluidizable solid material, to produce a substrate having a desired device shape, for instance a balloon shape, depositing a curable polymer-forming composition onto the outside of the shape. Spray, print or dip deposition may be used. After deposition, one can direct UV or other cure inducing energy at the deposited layer to cure the polymer in the device shape, followed by a fluidizing step to get rid of the fluidizable material.

In a further aspect, the invention pertains to a mold form for a medical device which is formed of a material which melts at a temperature below 100° C., preferably at or below 50° C., and especially at or below ambient temperature (about 22° C.).

In some embodiments the inventive process allows for varied fabrication techniques, for instance applying a liquid curable formulation to a substrate of fluidizable material pattern-wise or uniformly, and/or curing by irradiating pattern-wise, sequentially or uniformly, as appropriate to the device being built. The curable formulation can be varied on-the-fly to change the physical properties of the device as desired. Moreover, the substrate may be altered, for instance to change fluidization properties of melt point or solubility, or to leave behind material such as fibers which may provide desired bridging structures or other desirable connections between portions of the device through the volume occupied by the substrate.

In a further aspect, the invention pertains to processes for forming medical devices from radiation curable compositions which cure to form polyimide polymers below about 50° C.

The process also allows for tailoring of physical properties to the demands of the article being formed.

Other aspects of the invention are described in the detailed description below and in the claims.

BRIEF DESCRIPTION OF THE DRAWINGS

FIG. 1 is a perspective view of a balloon catheter using a balloon of the present invention.

FIGS. 2A-2C illustrate a preferred method of forming a dilatation balloon of the present invention.

DETAILED DESCRIPTION OF THE INVENTION

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

Some embodiments of the present invention are directed to processes for forming medical devices, especially those deployed and operated through various vascular channels, to devices obtained from such processes and to novel modified polyimide polymers useful therein.

Referring to FIG. 1 there is shown a catheter 10 comprising an elongated tube 12 with a balloon 14 mounted at the end thereof. The balloon is made of a cured polymeric material in accordance with the invention hereof.

Figure 2C:
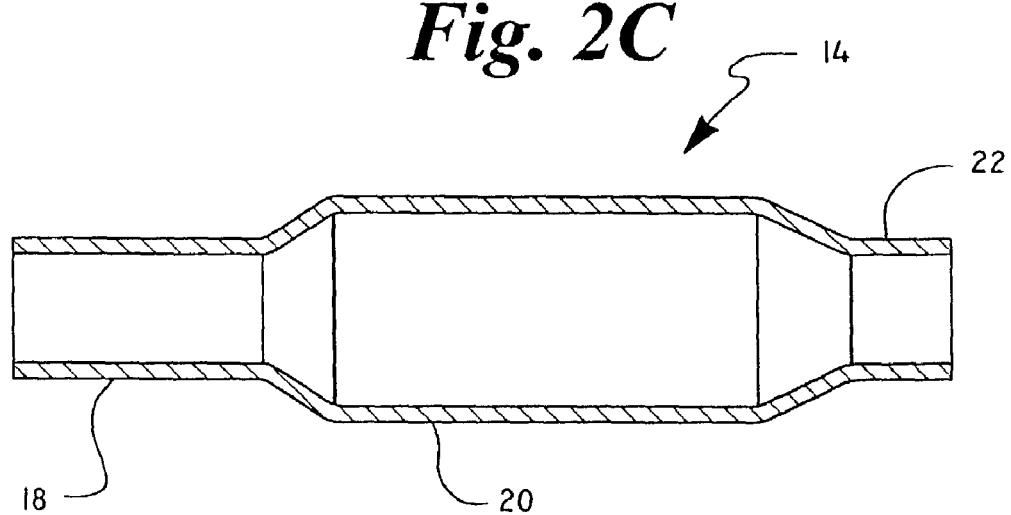

FIGS. 2A-2C illustrate one method of the present invention for forming a balloon 14. As shown in FIG. 2A, a substrate 30 is provided having an exterior surface of configuration which will determine the inner surface of balloon 14. This exterior surface configuration corresponds to the desired interior surface configuration of balloon 14 when balloon 14 is fully inflated. In at least some cases the exterior surface of the substrate 30 will also substantially determine the outer surface of the balloon, since the polymerizable material applied thereto will typically be very thin. The substrate is made of a solid material which can be readily fluidized under conditions do not destroy the integrity of the formed device (here the balloon).

In preferred embodiments of the present invention, substrate 30 is ice or another meltable material, such as a wax, characterized by a melting point of about 100° C. or less, preferably about 50° or less. In some embodiments, however, higher melting points may be used, or the substrate material may be fluidizable by another mechanism such as dissolution with water or another solvent which does not substantially attack the formed device under the substrate fluidization conditions employed. An example of such a material is a water soluble polyvinyl alcohol (PVA) manufactured by Environmental Polymers of Irlam, UK, and sold under the trademark Depart™. Depart™ polymer compositions have melting temperatures of from about 185° C. and 210° C. and can be altered to become fully soluble in ambient to hot water, for instance 20-80° C. More detailed information on the Depart™ product can be found in Materials World, Vol. 10, No 8, pp 36-38, August 2002. Thus, references to ice and/or wax in specific embodiments herein should be taken to be illustrative embodiments which can be readily modified to employ alternate fluidizable materials such as the Depart™ PVA compositions and other readily fluidizable materials.

The substrate 30 may also be a composite material comprising solid particles which are not fluidizable, for instance strength reinforcing inorganic particles, in a solid matrix of fluidizable material. In some cases it will be desirable that, upon fluidization of the matrix material, the particulate material can be removed the formed device together with the matrix material. However, as described more fully herein, in some cases it may be desirable to leave behind non-fluidizable components of the substrate 30, such as fibers or other particulate material, when the fluidizable material is removed. When left behind such components can provide bridging structures between multiple layers or other features as described herein.

As shown in FIG. 2A, substrate 30 has a proximal waist section 34, a balloon section 36 of greater outside diameter, and a distal tip section 38 of reduced outside diameter.

As shown in FIG. 2B, film 40 of a radiation curable composition is deposited on the exterior surface of deposition substrate 30. This step can be performed, for example, by dipping deposition substrate 30 into a solution of the curable composition, or, if the composition has a low viscosity, into the neat composition, withdrawing the substrate 30, allowing the solvent to evaporate, if present, and then irradiating the resulting film to produce the cured film 40 on deposition substrate 30 at a temperature below the melting temperature of substrate 30. The curable composition may also be applied by spraying. Multiple depositions and cure steps may be used to build the thickness of the cured material to a desired thickness. In some embodiments, each deposition formed with this technique may be from about 0.00001 inches (0.25 μm) to about 0.001 inches (25.4 μm) thick, suitably about 0.0001 inches (2.5 μm) thick. In some embodiments of the present invention, repeated dip coatings and radiation curing is performed until the desired thickness of film 40 has been formed. For some balloon embodiments the final wall thickness may be on the order of about 0.0001 inches (2.5 μm) to about 0.002 inches (50 μm), for instance about 0.0002 inches to about 0.001 inches (5-25 μm). Other balloons may desirably have thicker or thinner walls, for instance if a balloon wall is formulated with a porous outer layer to carry and deliver a drug load, the desired total wall thickness might be substantially greater than 50 μm.

The next step in the process is the removal of deposition substrate 30 from within the cured polymer film 40. When the substrate material is fluidizable by melting, removal is preferably achieved by simply heating the assembly of deposition substrate 30 and cured film 40 to a temperature above the melting point of substrate 30. The deposition substrate melts and flows out leaving the cured film device. For instance if the substrate 30 is made of ice, the assembly may be heated by exposing it to ambient temperatures for a period of time. In the case where substrate 30 is fluidizable by selective dissolution, the assembly may be immersed in a suitable solvent for a period of time, and/or a solvent flow may be directed at the substrate to effect dissolution and removal of the substrate. The material used to form the substrate may be collected and reused if desired. Following removal of the substrate the desired device is obtained, in this case a balloon.

The substrate 30 may be readily formed by filling a corresponding female mold with water or melted wax and then lowering the temperature below the freezing point of the substrate material employed. Forming the deposition substrate 30 from ice or wax provides many advantages over the process employed in U.S. Pat. No. 4,952,357 to form polyimide balloons. The substrate material is cheaper, more easily recycled, and no toxic or corrosive material is needed.

The present invention has several important advantages in at least some embodiments. First, it offers extremely thin walls, and therefore is extremely well suited for low profile catheters and balloons. Second, the process of the present invention, as illustrated in FIGS. 2A-2C, offers close control over the inside diameter tolerances of balloon 14. Third, the method of the present invention, unlike other balloon fabrication techniques, can be used to obtain desired wall thickness profile desired, whether that be thinner cones, relief patterned surfaces or the like. Fourth, the method can be used to optimize the properties of the polymer material deposited for different areas of the device. Fifth, very complex device structures can easily be produced.

Figure 3A:
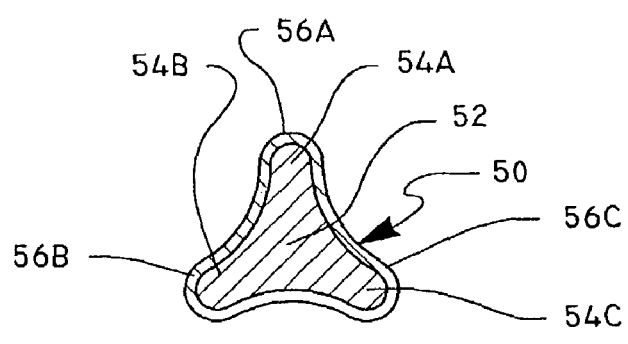
FIGS. 3A and 3B illustrate a balloon formed in a normal deflated state and inflated in a pressurized state.
Figure 3B:
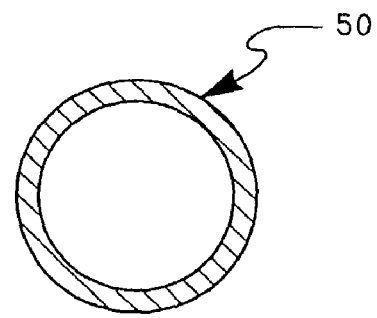

In the embodiment of the method of the present invention described in FIGS. 2A-2C, substrate 30 has a surface configuration which corresponds to the desired shape of the balloon in a fully inflated condition. Conversely, the surface configuration of substrate 30 can correspond to the desired shape of the balloon in a deflated condition (or in a partially inflated condition). This latter embodiment is particularly advantageous for ensuring that the balloon has a minimum profile when deflated by making the shape of the deflated balloon predictable. By using this embodiment, creasing and heat setting characteristics may not be required. FIGS. 3A and 3B illustrate an example of this embodiment. FIG. 3A is a cross section of balloon 50 in a deflated condition, which has been defined by substrate 52 having three lobes 54A-54C. As a result, balloon 50 has three corresponding lobes 56A-56C when deflated. FIG. 3B shows the fully inflated state of balloon 5.

The ice or wax form can also be prepared by mechanical or thermal processing of a body of such material, such as a rod or cube shape, into the desired balloon or other shape. For instance, both ice and wax, at a suitable low temperature, can be readily sculpted mechanically or using a laser.

Considering all of the foregoing, balloons may be readily manufactured which have, for example, diameters of about 1.5-25 mm, lengths of about 5-200 mm, wall thicknesses of about 0.0003-0.03 inches, in some embodiments from about 0.0003-0.003 inches, and to any of the typical ranges for balloon dimensions and strengths as typically utilized in the medical industry heretofore.

For any given catheter construction, the balloon may be bonded to a shaft which may be formed of polyester, polyamide such as nylon 10, nylon 6/10, nylon 11 nylon 12, or mixtures there of, polyethylene, thermoset polyimide, polyetheramide block copolymer, such as the ester-linked polyetheramides sold under the trade mark PEBAX®, polyetherester block copolymer such as sold under the ARNITEL® and HYTREL® trademarks, or anything else known in the art. In another embodiment, however, the balloon may be formed integral with the shaft or a portion thereof.

Deposition techniques can be varied according to the characteristics desired. General dip and spray coating techniques may be used. Moreover, much more sophisticated techniques can be used. Using multiple layers to build up the balloon, the balloon can be provided with site specific characteristics while still providing a balloon whose overall property profile is not substantially comprised. For instance, in one embodiment the curable composition is applied with an applicator employing one or more computer controlled spray heads similar to ink jet print heads. Different curable formulations may be provided via multiple spray heads, allowing the cured formulation to be varied on-the-fly i.e., as it is being applied, in the manner of printing different colors. In this way, for instance the innermost layer of the waist area may be formulated to provide tacky cured properties which facilitate subsequent bonding to a shaft, while, in the expandable portion of the balloon, the same innermost layer is formulated to minimize tack so as to avoid blocking adhesion. Likewise, the outermost surface may be formulated to provide softness and/or lubricity without tackiness. In this way two or more different polymer blends may be created on-the-fly in order to create transitions within the balloon or other device in relation to stiffness, softness, hydrophilicity, tack, tensile strength, elongation and/or MRI for fluoroscopic visibility.

The cured outer layer polymer material may be rendered hydrophilic by using curable compounds having hydrophilic side-branch or main moieties. Such moieties may be anionic or cationic groups or polyethylene oxide blocks. This is particularly advantageous when the base resin property is generally very hydrophobic, as is true for instance for polyimides.

Accordingly, one can spray (using for example a high definition ultrasonic spray nozzle) spiral patterns of stiff polyester onto or into soft polyester to form a shaft. One can apply (e.g. by spray, dipcoat, brush, etc.) a nanoclay containing polymer in any pattern in conjunction to the same solution containing no filler. One can do the same using a radiopaque (Barium salt, Tungsten salt) or various magnetic substances, i.e. ferromagnetic, paramagnetic superparamagnetic, or diamagnetic substances (e.g. dysprosium or gadolinium salts). One can use 2, 3 or more curable compositions in any pattern (e.g. separated in axial (rings), circumference (stripes) or radial (layers) direction). Alternatively, or at the same time, one can also mix multiple polymers during spraying to obtain a gradual transition.

A very precise spray technology which can be used in the invention is by means of ultrasonic spraying. Suitable ultrasonic spray systems are available from Sono-Tek Corp., Milton NY, and are described at http://www.sono-tek.com/. Other technologies to make very precise lines or features are electrohydrodynamic printing, such as is available at Princeton University Ceramic Materials Laboratory and described at http://www.princeton.edu/~cml/html/research/ehdp.html; and picoliter dispensers described at http://www.microdrop.de/html/about.html and available from Microdrop GmbH, Norderstedt Germany.

Besides being suitable for applying the radiation curable composition, these techniques can be employed to modify the fluidizable form before application. For instance, structures can be made in ice on top of the a more basic ice form and the result employed as the substrate which is then covered by the radiation curing formulation. In this way basic forms can be easily modified to provide a variety of products with different structural features. A particular example has as its objective a balloon having a bumpy surface and a uniform wall thickness. A standard balloon mold ice form prepared in accordance with the invention can be modified by applying bumps to the surface at specific locations using water in a subfreezing environment. Subsequent application of a radiation curable formulation to the modified ice-form, followed by curing, can be employed to provide the objective balloon.

The spraying process allows the precise definition of the wall thickness on all sides of the balloon and, as such, one can achieve an even wall thickness in cone, and central section or even a thinner wall thickness in the cone section. To spray with accurate precision (spatial as well as allowing rapid changes in flow rate) one can use ultrasonic spray nozzles as described above.

The substrate shapes can be made in a polytetrafluoroethylene (PTFE) coated clampshell mold, over a similarily coated corewire, or by any other suitable means. By including a metal central corewire through an ice shape, one can use electrostatic spraying as a means to get a very homogeneous layer. A metal core wire can also be used as a resistance heater to facilitate melting of the form after the device has been formed and cured.

One way to include an axial reinforcement in the device being formed is to spray more material along several stripes parallel to the central axis. Such stripes can be used to reinforce the longitudinal balloon body region under the blade pad of a cutting balloon as described in U.S. Pat. No. 5,320,634, Vigil et al, for example.

The process can also be used to produce preform shapes of balloon parisons, where the parison would be used in a conventional blow molding step. Ideal balloon preform shapes and preferential thicknesses could be achieved by multiple step spraying of the polymer coating.

Composites may also be prepared by the inventive processes. For instance:

Spiral or coil wind a wire or fiber made out of SPECTRA®, KEVLAR® or other, polyimide, polyester, ultra high molecular weight polyethylene, glass, flexible ceramic, or metallic material around a balloon shaped ice or wax form, and then spray on the photocurable composition and cure. In some embodiments an underlayer of the photocurable composition is applied and cured first.

Small stripes of a stiff material may be put onto the ice or wax, keeping them in place by mechanically pining, e.g. using push pins at the end, or by making the stripe material wet on the inside so that it freezes against the mold, spraying the photocurable composition, and curing to produce a shape in which the stripe is embedded in the balloon or other device being formed.

A braided sock made out of a fiber material can be slid over the ice or wax form, or over a cured layer already applied to the form, followed by spraying and photocuring.

Strips of "Bucky" paper, made out of carbon nanotubes, may be laid on the ice or wax form, or over a cured layer already applied to the form, followed by spraying and photocuring.

As, already noted, various fillers, optionally functionalized, may be included in the polymer composition. The filler particles may have a fibrous, spherical, plate-like, or amorphous shape. Radiopaque and paramagnetic materials are among the types of fillers which may be used. Reinforcing particles may be employed. Particles of carbon, clay, silica, alumina, or liquid crystal polymer, are examples. Nanofillers, for instance nanoclays, nano ceramics and carbon nanofibers and tubes, characterized by a diameter of about 100 nm or less, are particular examples. Such particles are sufficiently small that they do not substantially reduce optical clarity of the composition and will not obstruct the passage of UV light through the solution as they are smaller then the wavelengths being used.

With conventional thermoplastic polymer processes it is very difficult to obtain a high dispersion of nanoparticles. In the case of the present invention where very low viscosity compositions may be employed, the mixing and dispersion can be accomplished much easier.

Drugs may be incorporated into the curing formulations, directly or carried on the fillers. This will lock them in the polymer matrix after curing. As the curing is done at room temperature, a wide range of pharmaceutical substances may be used. Such substances may be localized on the device to specific tissue or fluid contact areas so as to maximize beneficial effects while minimizing side effects and/or compromising the physical properties of the device. Some drugs may be incorporated into the interior of fillers such as nanotubes, rather than, or in addition to, being incorporated thereon. Stents are particular examples of devices where drugs may be desirably incorporated.

Using multi-head spray printing techniques as described above, compositions comprising such reinforcing agents may be applied in a pattern-wise manner, with intervening space filled by relatively unreinforced compositions in order to provide the end product with a desired combination of physical properties such as balloon burst strength, burst profile, compliance, compliance curve profile, and elastic stress response.

The curing radiation is preferably UV source, that is one having a significant output in at least a portion of the range of about 150 to about 400 nm. Broad or narrow spectrum sources may be employed.

As an alternative to changing the formulation on-the-fly, or in addition thereto, cured properties may be modified by pattern-wise curing. For instance, a UV laser, or a focused broadband UV source, may be directed at a curable coating in an overlapping helical or mesh pattern until the entire layer has been cured. Curing in such a manner may substantially alter the physical properties of the layer relative to curing by applying the requisite irradiation in a substantially uniform manner.

After the composition has cured, the assembly is heated to melt and drain the water or wax form. In the case of ice forms, in order to get rid quickly of the water, one might use microwave heating, as the absorption rate of microwaves in water is much higher than for polymers.

Radiation curing formulations may also be utilized to produce complex devices on simple substrates. Stent devices are a particular example. Another example is a balloon having an outer surface which has a raised pattern to engage a stent during inflation so as to prevent slippage. Such complex structures can be obtained by pattern-wise application of one or more layers of curable material, using a pattern which leaves voids at appropriate positions, or by pattern-wise curing of a uniformly applied coating. Using optical systems and masks, one can cure only specific areas after which one can wash of the non-cured material in adjacent areas. Details to sub-micron level can be created as UV light can be focused to within this range. One way to get homogeneous illumination of a tubular structure is to focus a parallel expanded light beam into a conical mirror in which the tubular structure (balloon or shaft) is oriented along the central axis.

The following are specific modifications which may be employed in forming balloons:

A polyester or polyimide balloon can be produced with an equal wall thickness in core, cone and waist section using a spraying process in conjunction with dissolvable lost-wax mold made out of ice, wax, salt. After or during spraying one can irradiate with UV to form the polymer. Rotating the mold will cause the solvent to spread out.

Spraying stripes in a straight pattern or spiral can make a striped balloon. This for example could be used for the cutting balloon as they require material underneath the knives that doesn't extend in axial direction as this would break the adhesive bond between the blade and the polymer Outer surface bumps can be created at the transition of the cone and body of a balloon, spaced so as to be exposed when the balloon is deflated and folded for insertion into the vascular system of a patient. A stent can then be crimp mounted over the folded body portion between the bumps such that the bumps prevent the crimped stent from sliding off. By appropriate shaping, such bumps can also improve cross-ability of the catheter/balloon/stent assembly, e.g. by tapering the diameter from the folded balloon to the diameter of the crimped stent.

Also applicable to catheter/balloon/stent assemblies, a hydrophilic polymer forming composition can be sprayed and cured on the outer surface of the balloon cone sections while a hydrophobic polymer forming composition is used on the core section so as to improve stent securement.

Instead of producing a very smooth outer surface in the core section, one can also produce a textured pattern to improve stent securement. This can be done by for example by utilizing an ultrasonic spray nozzle which can spray little "dots" in a predefined pattern.

A multilayer balloon with a soft outer layer may be produced.

One can also spray a layer or a pattern on top of existing balloons made by conventional methods.

A tapered balloon or even a tapered curved balloon can be made quite easily.

Still further applications of the present invention include the following:

Imagewise patterned application of a curable composition on a solid tubular form of a fluidizable material, or patterned curing, may be used to prepare stents in accordance with the invention. The curable compositions used may include organic or inorganic reinforcing agents such as fibers or other particles of liquid crystal polymers, metals, carbon, nanotubes, silicas, or the like. Property profiles may be varied longitudinally or radially by altering compositions in accordance with the particular property profile desired.

Portions of a device, such as metal stent struts structures, may be applied to in the shape-form before application of the curable composition, or applied to a first cured layer before application of a second layer of curable composition over the structures. Upon curing, such structures become embedded in the formed device.

A tubular graft of continuous material may be formed on a tubular shape-form, but with reinforcing structures pattern sprayed into the graft material in a manner analogous to the balloon reinforcing strategy described above.

Figure 13:
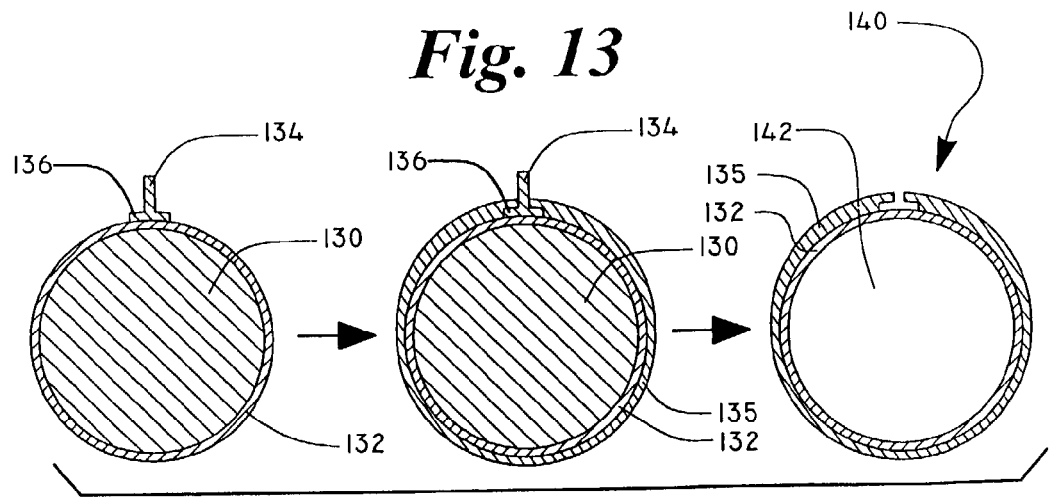
FIG. 13 is a schematic depiction of a process in accordance an embodiment of the invention, viewed in cross-section, for preparing a balloon having a chamber structure adapted to carry and dispense a drug at the treatment site.

Stent, graft or balloon structures may be provided with drug retaining chambers, for instance as described herein in connection with FIG. 13.

Polyester Stent grafts can be sprayed using this technology.

By incorporating low volatile nano- or micro-sized particles in the solution one is able to create porous structures. Heating the layer while UV-curing at the same time will force the volatile particles to form micro- or nano-channels to the surface. So one can use this to create a double layer balloon with a drug in between the two layers that is being forced out during expansion of the balloon. One can also spray such a layer on top of a drug containing polymer.

Catheter shafts can be formed using the same techniques and variations described for balloons. Consequently, one can produce both braided and non-braided shafts with different compositions of polymers, or having braided proximal portions and non- Thickness measurement during spraying and curing. It would be advantageous to build in a laser thickness measurement system during spraying to provide a feedback system. braided distal portions.

Figure 4:
FIG. 4 is a schematic side sectional view of a wire which may be used to prepare an ice or wax form mold useful for preparing a catheter shaft in the method of the present invention.

FIG. 4 depicts a wire 60 which may be used to generate a suitable shaft form. A layer of water or molten wax is applied to the wire, for instance by dip coating, and then cooled to solidify. This cycle may be repeated as needed to build up the form to the desire diameter, as shown at numeral 65 in FIG. 5. The radiation curing formulation is then applied and cured as described. Melting and removing the wax or ice form provides clearance to remove the wire. As an alternative to ice or wax forms, shafts can be sprayed directly on non-stick PTFE or silver coated mandrel wires.

Balloons and shafts can also be formed integrally, i.e., in one piece. FIG. 6 depicts an integral shaft and balloon form 70, obtained by placing the distal end of an ice or wax form 65 of FIG. 5 in a balloon-shaped mold form and molding the balloon form portion 75 thereover. The integral shaft and balloon are then formed over form 70 in the manner already described.

Tandem balloons can be prepared in a simple manner. Instead of one balloon form as shown in FIG. 6, the shaft form 65 may be modified to include two or more balloons form shapes, spraying and curing as before.

Figure 5:
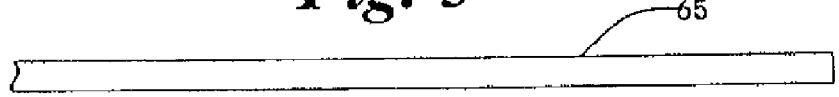
FIG. 5 is a view as in FIG. 4 with an ice or wax mold formed over the wire.
Figure 6:
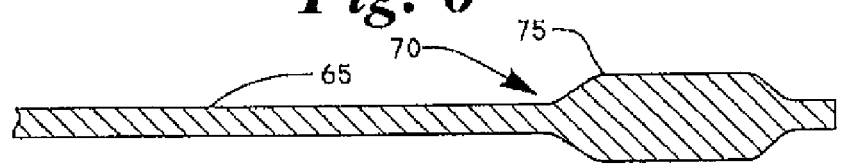
FIG. 6 is a view as in FIG. 5 with the form further modified to provide a balloon shape at the distal end.
Figure 7:
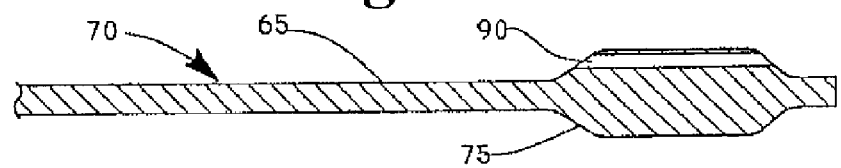
FIG. 7 is a view as in FIG. 6 with the form further modified to provide a longitudinal hole in the balloon form passing through the cone walls of the balloon form.
Figure 8:
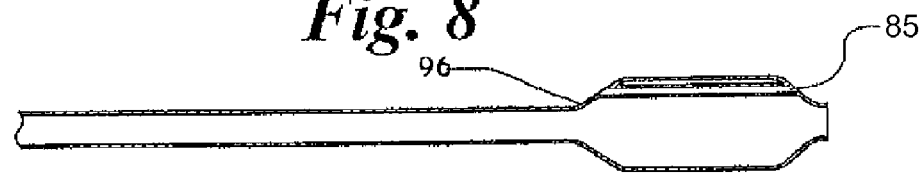
FIG. 8 is a side section view of a balloon for a rapid exchange catheter from the modified form of FIG. 8.
Figure 9:
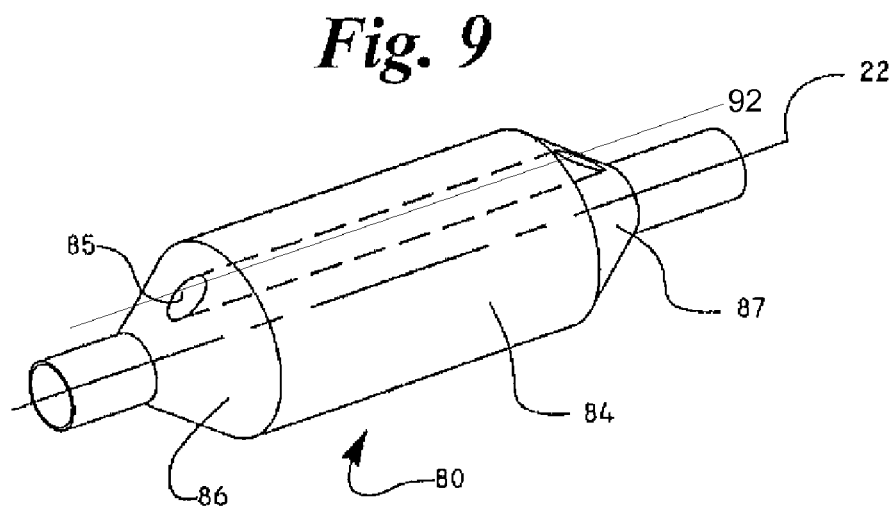
FIG. 9 is a perspective view of a balloon for a rapid exchange catheter which may be prepared in accordance with the invention.

FIGS. 7, 8 and 9 depict a more complex balloon form that can be prepared by modification of the form 70 of FIG. 5. This balloon can be used in a rapid exchange catheter system.

Current rapid exchange catheters entail two lumens over at least a portion of the catheter to provide fluid access to the balloon on the one hand and guidewire passage on the other hand. This dual lumen concept restricts the fluid access to and from the balloon chamber, which lead to increased inflation- and deflation times. It also adds to the overall profile of the system as there are four walls in cross section. Within patents U.S. Pat. No. 5,409,458 (Khairkhahan et al.) and U.S. Pat. No. 5,549,553 (Resseman, Stivland and Blaeser) two designs have been proposed to resolve this issue by attaching the guidewire lumen to the wall of the balloon. U.S. Pat. No.

5,409,458 shows a one-sided flattened balloon design were the guidewire lumen is glued against the exterior of the flat side. U.S. Pat. No. 5,549,553 shows a balloon in which the guidewire runs through part of the balloon wall. Both solutions are not ideal as they force the guidewire to one side of the balloon during inflation. This makes them both unsuitable to be used as stent deployment systems. First of all because the pressure they generate on the stent is non-uniform along the circumference, this due to the guidewire being forced between the balloon inflation chamber and the stent. Secondly, because of the guidewire being forced into the vessel wall by the balloon, the guidewire also presses into the vessel wall on both the distal as well as proximal side of the dilatation area during dilatation. Generally one wants a smooth transition between the distended region of the vessel and the undistended regions immediately distal and proximal thereto.

An alternative solution to the problem of designing balloons for rapid exchange catheters, especially those used to place stents, is a further aspect of the present invention. The inventive balloon has a guidewire channel 85 through the balloon as shown in FIG. 9. Instead of having the pressure chamber on one side of the guidewire, as in the above patents, FIG. 9 depicts a balloon 80, having a longitudinal axis 82, a central body portion 84 and proximal and distal tapering cone portions 86, 87. A longitudinal guidewire channel 85 is provided entering and emerging through the tapered cone walls 86, 87. A guide wire 92 is shown extending through channel 85. With this design the pressure chamber entirely surrounds the guidewire channel 85. Consequently, the pressure on the guidewire channel is equally exerted from all directions. Therefore the guide wire channel is not forced against the wall of the balloon during inflation and the pressure on the stent is equally distributed.

One way to produce such a balloon starts from a form as shown in FIG. 6. An axially extending hole 90, spaced radially out from the axis at a distance less than the outer wall is then drilled through the balloon portion 75 of ice form 70 to produce the modified form as shown in FIG. 7. Dipping or spraying the photocurable composition, and subsequent radiation curing produces a balloon 96 having an integrally formed off-axis longitudinal guidewire channel 95 85. Radiation curing of the photocurable composition may be accomplished, for instance, by irradiating through the ice form or by directing a beam obliquely along hole 90. Curing the composition film and melting the ice or wax will leave a balloon shape as shown in FIG. 8 where the wall of the balloon extends through the length of the hole. It is of course also possible to generate this hole during the production of the ice shape by having a wire in place during the freezing process and removing the wire later on. If one uses a metal wire for this, one can easily release it out of the ice shape by sending an electric current through it, heating the wire.

Another way to form the guide wire channel 85 of the balloon as in FIG. 9 uses a separately formed tube which is inserted into the hole 90 of the form 70 of FIG. 7 before the outside of the form 70 is coated and cured. Such tube may be formed in the manner described herein, or by any other means, and may be the same material as the rest of the balloon or a different material. The tube may be formed with fibers extending outward beyond the thickness of the tube at its ends in order to improve bond strength between balloon outer wall and the separately formed guide wire channel 85.

A balloon as in FIG. 9 formed by embedding a tube of some other material through the hole 90 prior to spraying may be desirable if one wishes to use the system as a stent delivery system. If the tube 95 is too thin or too elastic, it may be squeezed closed during crimping of a stent. If one integrates a tube out of some stiff material in the balloon construction, this potential problem can be overcome.

In a variation on the balloon of FIG. 9, more longitudinal channels through out the balloon are provided and left open such that the inflated balloon still allows the flow of blood through the system.

Spraying and curing the balloon also offers a way to produce the combined shaft and balloon construction in a single run. This can be done for example by taking a mandrel and producing a thin layer of ice or wax over the entire length. Secondly, the form of the balloon is added in ice on the end. The hole in the balloon shape as described above is drilled, and then the entire system is sprayed with the curable composition. Next one cures the composition and melts the ice or wax form.

Figure 10:
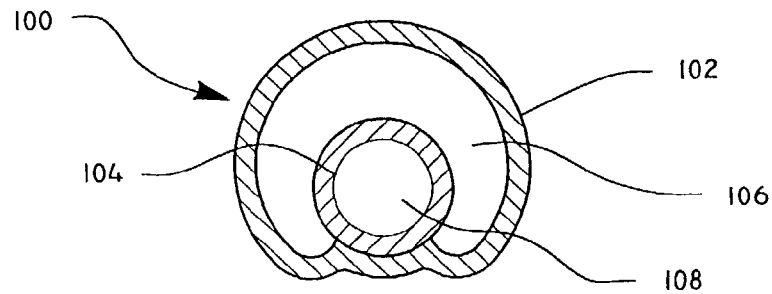
FIG. 10 is a cross-sectional view of a catheter shaft prepared in accordance with an embodiment of the invention.

In another embodiment of the invention, using a PTFE coated wire mandrel, with a moon-shape cross section, it is possible to prepare dual lumen shafts outer over a long length. Once more, a thin layer of ice is provided over the mandrel then a pre-formed tube forming the inner is placed in the inner rounding of the moon and the whole structure is sprayed with the curable composition and then cured. After melting the ice, the mandrel can be easily removed. FIG. 10 shows a section view of a shaft 100 produced in this way. The shaft has an outer wall 102, an inner wall 104, an outer lumen 106 and an inner lumen 108. The inner wall 104 is formed of the tube inserted into the moon curved substrate form, i.e. after the PTFE coated wire has been coated with the fluidizable substrate material, while the outer is formed of the subsequently applied UV cured polymer.

Figure 11A:
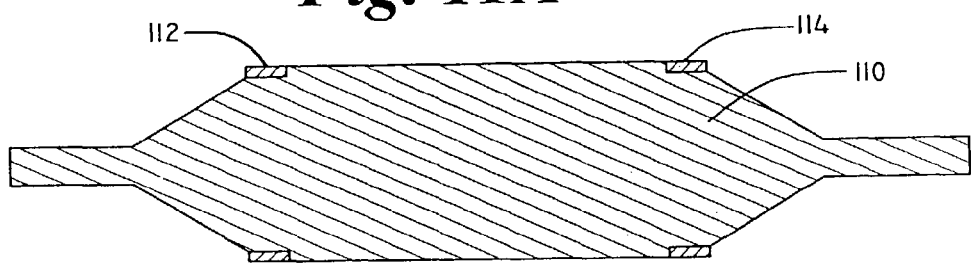
FIGS. 11A-C are side-section schematic views illustrating the steps of preparing a self-retracting balloon in accordance with an embodiment of the invention.
Figure 11B:
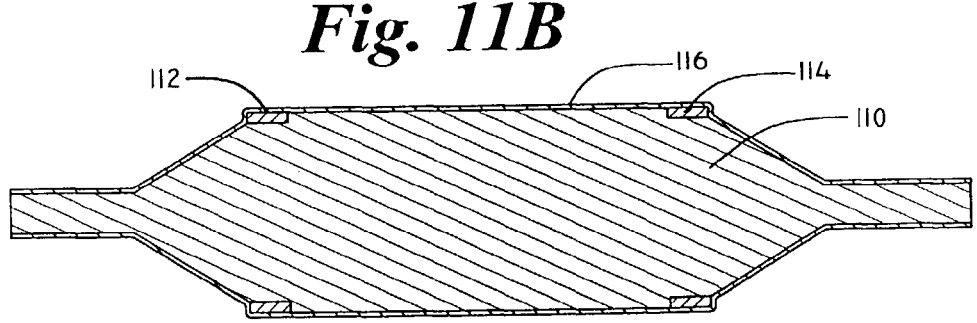
Figure 11C:
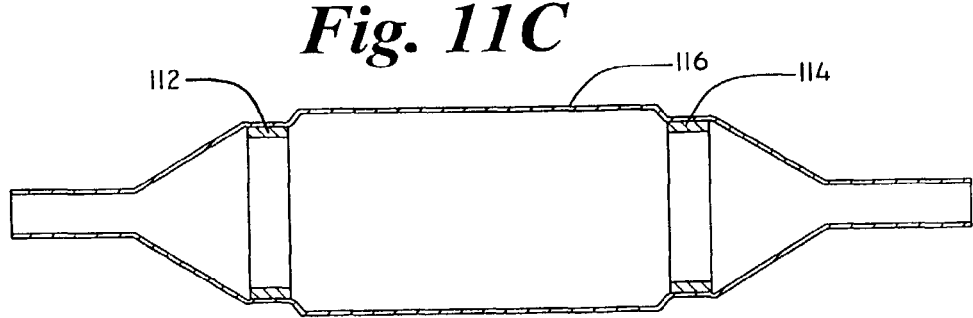

FIGS. 11A-C illustrate yet another embodiment of the invention. In FIG. 11A, a basic balloon form 110 of ice or other fluidizable solid is shown. To the form 110 have been applied a first polymer layer forming circumferential bands 112 and 114. The bands 112 and 114 are elastic materials which have been stretched from their rest diameter to reach their diameter on the form. The elastic material may be silicone or other rubbery material, but is one to which the cured polymer film formed of the curable composition will adhere. A second polymer layer formed from a curable composition 116 is then applied by spray or other technique, over the entire form, including over the bands 112 and 114, as shown in FIG. 11B, and then cured to form a balloon with the bands 112 and 114 embedded therein. In FIG. 11C, when the fluidizable form has been removed, the composite balloon is stressed by the bands 112, 114 to collapse to their rest position. This aids in obtaining a small deflated profile. Bands placed as depicted here, or in other configurations may also be used to alter balloon distension curves.

A modification of the balloon of FIG. 11C uses a first polymer layer, sprayed over the form and cured, before the bands 112, 114 are applied. Suitably, the bands employed in this embodiment are also over-coated and cured as described previously, so that they are encapsulated by the sprayed polymer. This technique avoids the necessity of maintaining a strong adhesive bond between the cured polymer forming the balloon body and the elastic bands. In further modifications of this balloon or the balloon of FIG. 11C, the bands 112, 114 may be made of a non-compliant material to change balloon compliance. The cured polymer forming the body of the balloon may be a compliant, semi-compliant or non-compliant material.

Figure 12A:
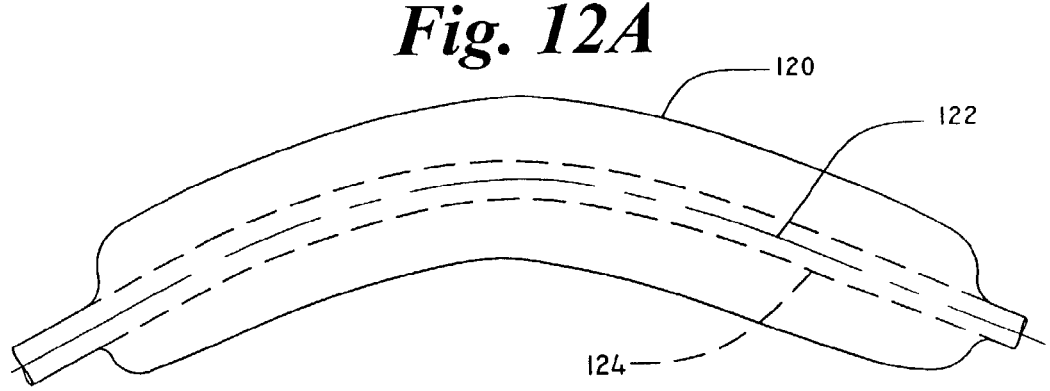
FIGS. 12A and 12B, respectively, show a side view of a balloon formed with an axial curve and an ellipsoid cross-sectional distal tube on which such balloon may be mounted.
Figure 12B:

FIGS. 12A and 12B depict another balloon embodiment which can be obtained in accordance with the invention. Instead of a symmetric balloon mold along the axial axis, balloon 120 is curved along the direction of the balloon axis 122. As most of the arteries are curved, this would actually be advantageous in many cases. One way to be able to direct the balloon and catheter shaft in the direction of the curvature of the vessel would be to use an ellipsoid shaped cross-section for the inner lumen 124, as shown in FIG. 12B. By going through a curvature this would align the shaft with the curvature.

Another embodiment of the invention uses a first ice shape mold, spraying at least a first layer over this ice layer and curing the layer(s) to form a proto-balloon. The ice form is then melted, but the water is kept in the proto-balloon and that water is actually pressurized to expand the proto-balloon to a second diameter. The expanded diameter can be only slightly larger than the diameter of the first ice-shape mold. Keeping the pressure on to maintain expanded diameter, the water is refrozen to fixate the expanded shape, after which at least one second layer is sprayed on the proto-balloon and cured. In this way one can build in a negative pressure in the balloon layer which would help to strengthen the balloon and allows creating different distension/pressure curves. The cycle of melting the form, pressurizing the cured balloon, refreezing the form material applying a further layer and curing the further layer may be repeated any number of times, until the desired balloon thickness is obtained. In this embodiment adhesion between the first and second layers can be enhanced if the first layer is formed with reinforcing fibers extending outwardly. Upon application and curing of the second layer, the fibers become embedded in both layers.

FIG. 13 schematically depicts another balloon-forming process according to the invention, in which the balloon is provided hollow chamber structures which can be used to carry and dispense drugs at a treatment site. After a first layer of curable composition has been applied to a substrate form 130 and cured to produce balloon inner layer 132, positive chamber forms 136 are applied to the balloon. A second layer 135 is then sprayed over the balloon covering the chamber forms except for stem regions 134, and cured. Layer 135 may be formed from the same or a different composition from that used to form the inner layer 136. After curing the second layer 135, the chamber forms are removed to yield a balloon 140 which includes hollow chambers 142 therein, opening to the outer surface. These pockets can be filled with one or more drugs prior to dilatation. During dilatation the drugs are squeezed out of the chambers as the balloon is pressurized against the vessel wall.

In another embodiment of the invention one can build a double layer balloon having a chamber between the two layers by depositing a first polymer-forming layer, curing the first layer, spraying an additional ice (wax) layer on top of the first polymer layer, covering the additional ice (wax) layer with a second polymer-forming layer, leaving open one or more channels for the water or wax to disappear, and then curing the second layer. In this way, one can build double layered balloons without a contact between the layers. Or if one only partly covers the first layers, one might create a contact point between the first and second layer, for example to fill with drugs etc. Fibers may be sprayed in the first polymer layer, the fibers being dimensioned so that they stick out of the first polymer layer. If one sprays a thin layer of water on the first polymer layer covering only part of the fibers (in other words, the fibers stick through the ice layer as well as the first polymer layer), and then sprays a top-polymer layer, a connection between the first and second polymer layer can be created. This technique can also be used with electrically conductive wires or fibers to provide electrical connection between separated layers.

In an example of a still further embodiment of the inventions described herein, one can incorporate long fibers in the ice mold that run from one surface to another part of the surface of an object and stick out on both ends. Spraying the polymer over this shape will embed the ends of the fibers in the polymer layer. Melting the ice will leave the fiber connection between the two points of the surface intact. One or more fibers can connect all kind of points between the surface. For example, providing a longitudinally extending stripe in the ice mold comprising fibers which extend 90 degrees with the longitudinal axis, and just beyond the ice mold surface at both ends of the fibers, followed by spray and cure of the curable formulation to embed the fibers in opposite ends will produce a balloon which grows from a circular shape to an elliptical shape when the pressure in the balloon further expands as the expansion in the fiber orientation is restricted.

In another example, a balloon similar to the previous example except that one connects all the fibers only on one end to the balloon surface, such that the fiber ends are incorporated into the balloon wall, while guiding the other end to the proximal section of the balloon. Following the same procedure one ends up with a balloon were a bunch of fibers sticks out on the proximal part of the balloon. These fibers may be connected to the catheter shaft, for example to a ring in the catheter shaft. The fibers are made out of a highly elastic material and are readily elongated under the during the inflation of the balloon. When the balloons is deflated, the fibers contract and they will help deflate the balloon. If fibers are distributed in the balloon wall at least predominately along a desired folding pattern, for instance along three or more longitudinally extending stripes, the fiber contraction will assist in refolding the balloon for safe retraction.

Alternatively, one could connect such single-end surface embedded fibers (non-compliant this time) all the way to the proximal side of the catheter, and allow the physician to determine the expansion of the balloon by connecting the fibers for example to a rotating device which would increase or decrease the length of the fibers as it is rotated. Depending on the number of fibers and their distribution along the surface, expansion characteristics of the balloon could be altered on the fly, to change balloon expanded diameters along a portion of the balloon length, e.g. to focalize dilation pressure over a smaller balloon length; to provide different cross sectional balloon configurations e.g. elliptical or polygonal cross-sections along some or all of the balloon length; to bend the balloon; and/or to control the balloon refold.

Another device can be built using the inventive method is a double layered balloon structure (using a first elastic layer, followed by an additional ice layer, followed by a second non-compliant layer, leaving a void between the two layers, which may optionally be supported by fiber connections between the layers, as previously described. Microchannels through the second layer may be formed-in-place or cut by UV-laser ablation. After removing the intermediate ice layer the resulting the intermediate chamber may be filled with encapsulated drugs. The encapsulation may be designed to break as a function of the external pressure. In other words, raising the internal pressure of the balloon would expand the elastic inner membrane against the outer non-compliant balloon, squeezing the intermediate drug layer. Once the pressure would pass a certain threshold, the encapsulation would snap and release a burst of the drug that would be injected in the vessel wall through the micro-channels. Of course one could use multiple drugs in multiple types of spheres exploding at different pressure levels.

Figure 14:
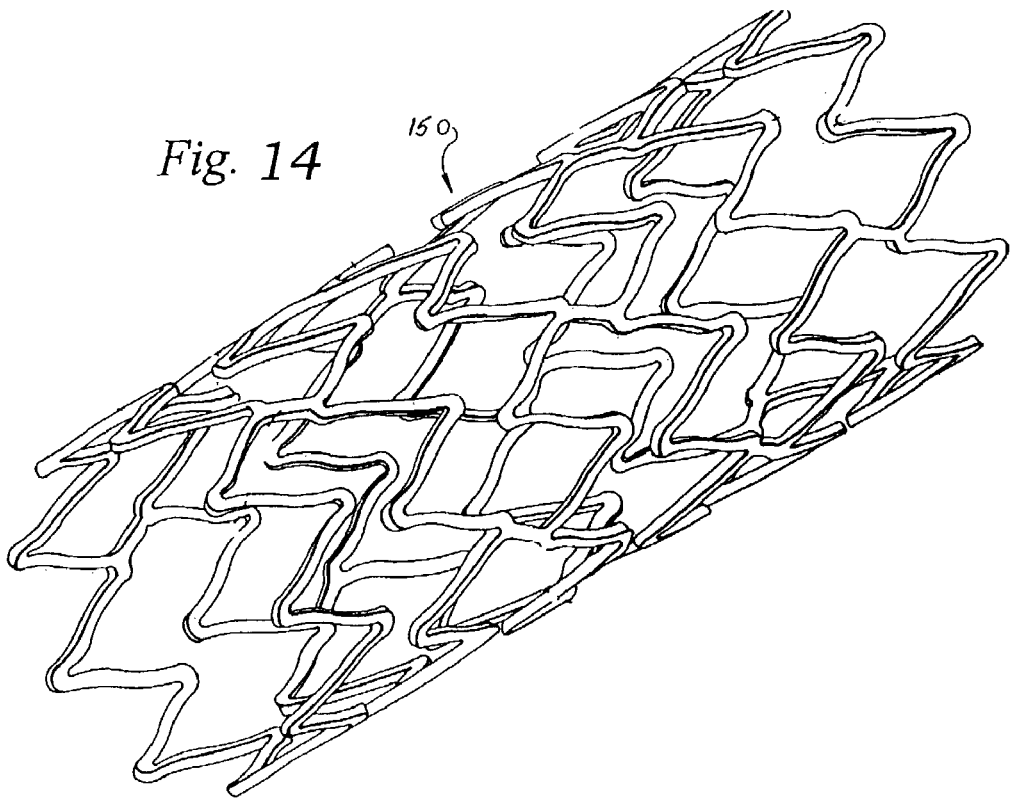
FIG. 14 is a perspective view of a stent in expanded configuration which may be made in accordance with the invention.

FIG. 14 depicts a stent 150 in expanded form. The stent may be formed on a shape form of ice or other fluidizable material, e.g. by imagewise spraying of a curable composition on a tubular form, followed by curing the sprayed composition. The stent material may be a composite as previously described.

As previously described, the invention may use a composition which is radiation curable to a solid polymer at a temperature below the melting point of the fluidizable substrate form material, suitably less than 100° C. In the case of ice forms, the material should be radiation curable below 0° C. Radiation curing compositions of (meth)acrylate esters (i.e. acrylates, methacrylates and mixtures thereof) are well known and may be used in the invention. A wide variety of cured properties are available from such compositions. Unless e-beam sources are used, such compositions typically employ a photoinitiator.

The radiation curable compounds, such as those which are initiated with UV or visible light radiation, may be monomeric, oligomeric, prepolymeric, or polymeric in nature. Mixtures of such compounds are typically used. Typically the compositions are liquids prior to curing in order facilitate application of the composition, and then a solid after being exposed to radiation such as UV or visible light radiation.

Examples of (meth)acrylate terminated radiation curable compounds include, but are not limited to, epoxy (meth) acrylates, urethane (meth)acrylates (aliphatic and aromatic), polyester (meth)acrylates, acrylic (meth)acrylates, polycarbonate (meth)acrylates and so forth and mixtures thereof. For spray application, low viscosity compositions are preferred, suitably viscosities of about 350 mPa·s or less, preferably about 150 mPa·s or less. When higher viscosity components are used, reactive monomer diluents and/or non-reactive solvents may be used to reduce the viscosity of the overall composition. Higher viscosity compositions can be used with other application techniques such as dip or brush coating.

The (meth)acrylate functional monomers typically range in molecular weight from about 86 to about 500 and typically have viscosities of 200 mPa·s or less at 25° C. It may be desirable to employ monomers in combination with oligomers to provide desirable coating viscosities. When such monomers are employed in combination with oligomers, they co-polymerize with the oligomers and form an integral part of the cured coating. Generally acrylate monomers are preferred over methacrylate monomers for radiation curing. Other radiation curable ethylenically unsaturated monomers can of course also be used alone or in mixture with (meth)acrylate monomers.

Ethylenically unsaturated oligomers and prepolymers which may be employed are typically viscous liquids at room temperature, with viscosities which range from a few thousand to greater than one million mPa·s at 25° C. They typically have up to 20 acrylate groups per molecule, with two to six acrylate groups per molecule probably the most common, and range in molecular weight from about 500 to about 20,000, but can be as high as 200,000 g/mol. Oligomers typically provide film properties which are superior to what can be achieved with monomers. Oligomers typically include a carbon containing backbone to which the radiation-curable functional group(s) is bound. Examples of suitable carbon-containing backbones include, but are not limited to, polyolefins such as polyethylene, polyesters, polyamides, polycarbonates, polyurethanes, and so forth. The size of the carbon-containing backbone can be selected to provide the desired molecular weight.

Other suitable UV curable compositions include cationically polymerizable compounds, most notably epoxies. Examples of commercially available suitable UV curable epoxies include, but are not limited to, UVACURE® 1500, 1530 and 1534 available from UCB Radcure, SARCAT® K126 available from Sartomer, and so forth. Vinyl ethers and styryloxy ethers are other cationically polymerizable compounds which can be used.

Photoinitiators are advantageously employed in combination with the radiation curable compounds. Photoinitiators typically form free radical species when exposed to UV light. Photoinitiators are typically used in amounts of about 0.5 wt. % to about 15 wt. % of the UV formulation, more typically about 0.5 to 10%, desirably 1 to 7% and more desirably 3-5% by weight of the composition. Typically this amount will be based on the binder composition, particularly if the binder composition is prepared prior to mixing with the magnetic material.

The photoinitiators are typically active in the UV/visible range, approximately 250-850 nm, or some segment thereof. Examples of photoinitiators, which initiate under a free radical mechanism, include benzophenone, acetophenone, chlorinated acetophenone, dialkoxyacetophenones, dialkylhydroxyacetophenones, dialkylhydroxyacetophenone esters, benzoin, benzoin acetate, benzoin alkyl ethers, dimethoxybenzoin, dibenzylketone, benzoylcyclohexanol and other aromatic ketones, acyloxime esters, acylphosphine oxides, acylphosphonates, ketosulfides, dibenzoyldisulphides, diphenyldithiocarbonate and diphenyl(2,4,6-trimethylbenzoyl) phosphine oxide.

The photoinitiators that may be used in combination with the radiation curable compound include photoinitiators available commercially from Ciba-Geigy Corp., Tarrytown, N.Y. under the "IRGACURE" and "DAROCUR" tradenames, specifically "IRGACURE" 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone) (e.g., "IRGACURE" 651), 1700 (the combination of bis(2,6-dimethoxybenzoyl-2,4-,4-trimethyl pentyl phosphine oxide and 2-hydroxy-2-methyl-1-phenyl-propan-1-one) and "DAROCUR" 1173 (2-hydroxy-2-methyl-1-phenyl-1-propane) and 4265 (the combination of 2,4,6-trimethylbenzoyldiphenyl-phosphine oxide and 2-hydroxy-2-methyl-1-phenyl-propan-1-one); photoinitiators available commercially from Union Carbide Chemicals and Plastics Co. Inc., Danbury, Conn. under the "CYRACURE" tradename, such as "CYRACURE" UVI-6974 (mixed triaryl sulfonium hexafluoroantimonate salts) and UVI-6990 (mixed triaryl sulfonium hexafluorophosphate salts); and the visible light [blue] photoinitiators, dl-camphorquinone and "IRGACURE" 784DC. Of course, combinations of these materials may also be employed herein.

If cationically polymerizable compounds are employed in the radiation curable composition the photoinitiator is suitably a cationic photoinitiator, a number of which are commercially available.

The above lists are intended for illustrative purposes only and are not intended to limit the scope of the present invention. Such UV curing systems are known in the art.

Alternatively, x-ray, gamma ray or electron beam curing may be employed. While a photoinitiator is typically employed in the case of UV curing, it is usually not required when such high energy sources are employed to cure the composition.

Another type of formulation which may be utilized in the invention is a photo-activated Diels-Alder addition reaction of an aromatic 2,5-dialkyl-1,4-diketone and a compound having two or more (meth)acrylate or maleimide groups thereon, optionally with a chain terminating mono-maleimide, or (meth)acrylate as illustrated by the following equation (I):

(I)

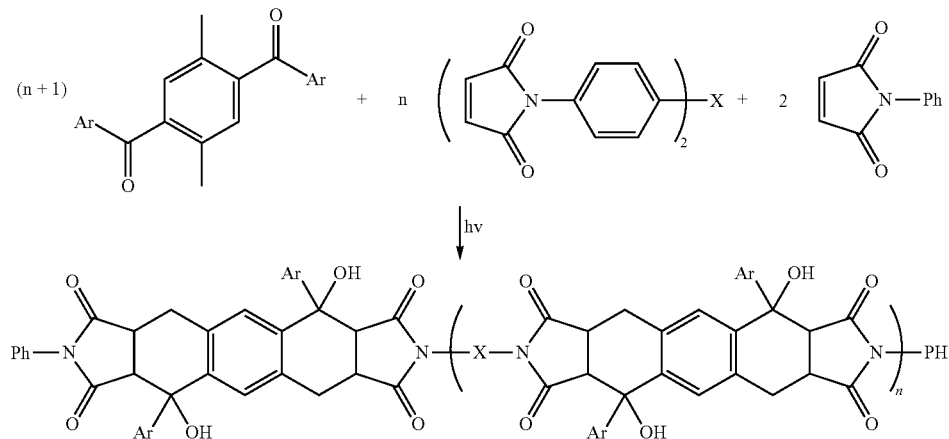

wherein X is a carbon linked organo group and Ar is an optionally substituted aromatic moiety. X may comprise an aromatic group or an aliphatic group, and may also contain hetero atoms such as O, N, S, P, Cl, F and Si. X also may be a polymeric moiety. Examples of X groups which can be used are arylene such as 1,3-phenylene, 1,4-phenylene,

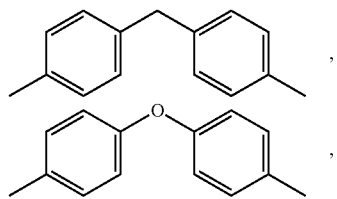

and substituted versions thereof; alkylene such as methylene, ethylene, propylene, butylene, 1,6-hexamethylene, polyethylene, polypropylene, and the like; alkylenearalkylene such as methylenephenylenemethylene; alkyleneetheralkylene. Examples of polymeric moieties include alkylene started polyethers, in which the polyether is an aliphatic polyether moiety, for instance polyoxyethylene $(EO)_n$ polyoxypropylene $(PO)_n$, polyoxybutylene and copolymers thereof such as $(EO)_n(PO)_m$, where n and m are positive numbers. X may also be a carbon linked aromatic polyether moiety, aromatic or aliphatic polyester, aromatic or aliphatic polyamide, polyurethane, polyorganosiloxane, copolymers, especially block copolymers of any of the above.

Specific bismaleimide compounds which may be employed include N,N'-m-phenylene bismaleimide, N,N'-ethylenebismaleimide, hexamethylenebismaleimide, N,N'-dodecamethylenebismaleimide, N,N'-m-xylylenebismaleimide, N,N'-p-xylylenebismaleimide, N,N'-1,3-bismethylenecyclohexanebismaleimide-, N,N'-1,4-bismethylenecyclohexanebismaleimide, N,N'-2,4-tolylenebismaleimide, N,N'-2,6-tolylenebismaleimide, N,N'-3,3-diphenylmethanebismaleimide, N,N'-4,4-diphenylmethanebismaleimide, 3,3-diphenylsulfonebismaleimide, 4,4-diphenylsulfonebismaleimide, N,N'-4,4-diphenylsulfidebismaleimide, N,N'-p-benzophenonebismaleimide, N,N'-diphenylethanebismaleimide, N,N'-diphenyl ether bismaleimide, N,N'-(methylene-ditetrahydrophenyl)bismaleimide, N,N'-(3-ethyl)-4,4-diphenylmethanebismaleimide, N,N'-(3,3-dimethyl)-4,4-diphenylmethanebismaleimide, N,N'-(3,3-diethyl)-4,4-diphenylmethanebismaleimide, N,N'-(3,3-dichloro)-4,4-diphenylmethanebismaleimide, N,N'-tolidinebismaleimide, N,N'-isophoronebismaleimide, N,N'-p,p'-diphenyldimethylsilylbismaleimide, N,N'-benzophenonebismaleimid- e, N,N'-diphenylpropanebismaleimide, N,N'-naphthalenebismaleimide, N,N'-m-phenylenebismaleimide, N,N'-4,4-(1,1-diphenyl-cyclohexane)-bismaleimide, N,N'-3,5-(1,2,4-triazol)-bismaleimide, N,N'-pyridine-2,6-diylbismaleimide, N,N'-5-methoxy-1,3-phenylenebismaleimide, 1,2-bis(2-maleimidoethoxy)ethane, 1,3-bis(3-maleimidopropoxy)propane, N,N'-hexamethylene-bis-dimethylmaleimide, N,N'-4,4'1-(diphenyl ether)-bis-dimethylmaleimide, N,N'-4,4'-(diphenylsulfone)-bis-dimethylmaleimide, N,N'-bismaleimide of N,N'-4,4'-(diamino)-triphenylphosphate or the like; an aromatic bismaleimide compound such as 2,2-bis[4-(4-maleimidophenoxy)phenyl]propane, 2,2-bis[3-chloro-4-(4-maleimidophenoxy)phenyl]propane, 2,2-bis[3-bromo-4-(4-maleimidophenoxy)phenyl]propane, 2,2-bis[3-ethyl-4-(4-maleimidophenoxy)phenyl]propane, 2,2-bis[3-propyl-4-(4-maleimidophenoxy)phenyl]propane, 2,2-bis[3-isopropyl-4-(4-maleimidophenoxy)phenyl]propane, 2,2-bis[3-butyl-4-(4-maleimidophenoxy)phenyl]propane, 2,2-bis[3-sec-butyl-4-(4-maleimidophenoxy)phenyl]propane, 2,2-bis[3-methoxy-4-(4-maleimidophenoxy)phenyl]propane, 1,1-bis[4-(4-maleimidophenoxy)phenyl]ethane, 1,1-bis[3-methyl-4-(4-maleimidophenoxy)phenyl]ethane, 1,1-bis[3-chloro-4-(4-maleimidophenoxy)phenyl]ethane, 1,1-bis[3-bromo-4-(4-maleimidophenoxy)phenyl]ethane, 1,1-bis[4-(4-maleimidophenoxy)-phenyl]methane, 1,1-bis[3-methyl-4-(4-maleimidophenoxy)-phenyl]methane, 1,1-bis[3-chloro-4-(4-maleimidophenoxy)-phenyl]methane, 1,1-bis[3-bromo-4-(4-maleimidophenoxy)-phenyl]methane, 3,3-bis[4-(4-maleimidophenoxy)phenyl]-pentane, 1,1-bis[4-(4-maleimidophenoxy)phenyl]propane, 1,1,1,3,3,3-hexafluoro-2,2-bis[4-(4-maleimidophenoxy)-phenyl]propane, 1,1,1,3,3,3-hexafluoro-2,2-bis[3,5-dimethyl-(4-maleimidophenoxy)phenyl]propane, 1,1,1,3,3,3-hexafluoro-2,2-bis[3,5-d]bromo-(4-maleimido-phenoxy)phenyl]-propane and 1,1,1,3,3,3-hexafluoro-2,2-bis-[3- or 5-methyl-(4-maleimidophenoxy)phenyl]propane, etc.

The aromatic 2,5-dialkyl-1,4-diketone used in the reaction of equation (I) may also be varied widely in structure. Ar may be the same or different and may be for instance phenyl and substituted phenyls, e.g. R—$C_6H_4$—, where R is alkyl, alkoxy, cyano, fluoro, hydroxyalkyl, and the like, and the alkyl and alkoxy groups may have for instance 1-20 carbon atoms, optionally interrupted with one or more ether oxygen atoms. Ar may also be naphthyl and substituted naphthyl. Specific Ar groups may be hydroxymethylphenyl, dimethoxyphenyl, diethoxyphenyl, dodecylphenyl, dodecyloxyphenyl, 2-hydroxyethoxyphenyl, and mixtures of these. In some cases it may be possible to substitute an aliphatic group, for instance a 1-hydroxycyclohexyl group at the Ar positions.

In equation (1) some or all of the bismaleimide compounds may be replaced with compounds having three or more maleimide groups, examples of which include, polyfunctional maleimide compounds obtained by the reaction of maleic anhydride with polyamine condensation products obtained by reacting aniline and formalin, 3,4,4'-triaminodiphenylmethane, triaminophenol, tris-(4-aminophenyl)-phosphate, tris(4-aminophenyl)-phosphate, tris(4-aminophenyl)-thiophosphate, or other polyamines.

(Meth)acrylate and acrylamide compounds may also be substituted for some or all of the maleimide compounds depicted in equation (1). When compounds having multiple (meth)acrylate groups are employed, the product is a polyester, rather than a polyimide. Similarly if acrylamide compounds are employed the product is a polyamide. Copolymers may be produced from mixtures of bismaleimides with multi (meth)acrylates and/or multiacrylamides.

Suitably the composition is formulated to have a ratio of equivalents of maleimide and/or (meth)acrylate groups to diketone compounds of from about 1:1 to about 4:1, more preferably about 1:2.

The group X may be modified to provide a softer, more flexible cured polymer than has heretofore been available from conventional polyimides. In particular, longer chain alkylene or (poly)alkyleneoxy groups as X groups will enhance flexibility and elongation properties of the polymer and may also provide improved softness. Longer chain alkylene or (poly)alkyleneoxy groups on the Ar moiety should also improve softness. Combining maleimide compounds having different X groups and/or using combinations of aromatic diketones allows for the properties of the cured polymer to be modified such that flexibility, toughness and strength can be optimally balanced.

While the traditional polyimides have been noted for their strengths properties, high temperature performance has been considered a major feature of the commercially available polymers. Hence they have traditionally been prepared with very low to no heteroatom content outside of the imide rings and aromatic rings and with very high aromatic content. For the present invention the device manufacturer can tailor the properties of the cured properties either by selection of the bismaleimide, selection of the aromatic diketone or by blending of materials or any combination thereof.

As an alternative to radiation curing, a composition which is curable upon mixing of two or more components may be employed, the individual components being stable until mixed. The individual components may be blended on-the-fly, so that the resulting composition cures promptly as it is applied, but does not cure in the application apparatus.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication and/or claim presentation timing requirements, any dependent claim which follows should be taken as alternatively written in a multiple dependent form from all prior and subsequent claims which possess all antecedents referenced in such dependent claim if such multiple dependent format is an accepted format within the jurisdiction (e.g. each claim depending directly from claim 1 should be alternatively taken as depending from any previous claims). In jurisdictions where multiple dependent claim formats are restricted, the subject matter of the dependent claims should each be also taken as alternatively written in each singly dependent claim format which creates a dependency from a prior or subsequent antecedent-possessing claim other than the specific claim listed in such dependent claim below.

The invention claimed is:

1. An article comprising a multi-layer polymeric material film comprising at least first and second layers, each layer having an inner and an outer surface, said first and second layers being directly bonded to each other over a coextensive area along respective outer and inner surfaces, each of said first and second layers having an at-rest configuration defining an at-rest area on said respective outer and inner surfaces corresponding to said coextensive area, the at-rest area of said first layer outer surface being smaller than the at-rest area of said second layer inner surface, the at-rest configuration being when said respective outer and inner surfaces are unstressed.

2. An article as in claim 1 wherein said article is a medical device.

3. An article as in claim 1 wherein said article is a dilatation balloon and said film is the balloon wall.

4. A dilatation balloon as in claim 3 wherein said balloon wall has generally coplanar inner and outer surfaces, said coextensive area is a region between, and generally coplanar with, the inner and outer balloon wall surfaces.

5. A dilatation balloon as in claim 4 wherein said coextensive area extends over substantially the entire balloon wall.

6. A dilatation balloon as in claim 4 wherein said coextensive area is a region which extends over less than the entire the balloon wall.

7. A dilation balloon as in claim 6 wherein one of said layers is an elastomeric band which has been stretched from an at rest configuration prior to inclusion thereof within the balloon wall.

8. The article of claim 1 wherein said first layer is an inner layer and said second layer is an outer layer.

9. The article of claim 1 wherein said first layer is an outer layer and said second layer is an inner layer.

* * * * *